United States Patent [19]

Suzuki

[11] Patent Number: 4,761,181

[45] Date of Patent: Aug. 2, 1988

[54] METHOD FOR STABILIZING ORGANIC BASE SUBSTANCES TO LIGHT

[75] Inventor: Yoshiaki Suzuki, Minami-ashigara, Japan

[73] Assignee: Fuji Photo Film Co., Ltd., Kanagawa, Japan

[21] Appl. No.: 6,364

[22] Filed: Jan. 23, 1987

[30] Foreign Application Priority Data

Jan. 24, 1986 [JP] Japan ................................. 61-13396

[51] Int. Cl.$^4$ ............................................. C09D 11/00
[52] U.S. Cl. ........................................ 106/22; 106/20; 106/26; 430/372; 524/84; 549/3
[58] Field of Search ............................ 106/20, 22, 26; 430/372; 524/84; 549/3

[56] References Cited

U.S. PATENT DOCUMENTS

| | | | |
|---|---|---|---|
| 3,432,300 | 3/1969 | Lesfina et al. | 430/379 |
| 4,111,857 | 9/1978 | Engler et al. | 549/3 |
| 4,306,875 | 12/1981 | DeFeo et al. | 106/22 |
| 4,505,749 | 3/1985 | Kanekiyo et al. | 106/20 |
| 4,590,288 | 5/1986 | Klemann | 549/3 |

FOREIGN PATENT DOCUMENTS 0087649 7/1975 Japan .
1496506 12/1977 United Kingdom .

*Primary Examiner*—Paul Lieberman
*Assistant Examiner*—Willie J. Thompson
*Attorney, Agent, or Firm*—Birch, Stewart, Kolasch & Birch

[57] ABSTRACT

An organic base substance having an absorption maximum in a range of about 300 nm to about 1,500 nm is stabilized by making it coexist with a specific dithiolato metal complex. Fastness to light of dyes can be remarkably enhanced.

16 Claims, No Drawings

METHOD FOR STABILIZING ORGANIC BASE SUBSTANCES TO LIGHT

BACKGROUND OF THE INVENTION (1) Field of the Invention

This invention relates to stabilization of organic base substances to light.

(2) Description of the Prior Art

It is widely known that organic base substances, e.g. organic dyes, generally tend to fade or discolor by the action of light. In the field of ink, dyeing of fibers, or color photography, studies have been made to prevent the fading or discoloration of organic dyes or to improve fastness to light.

Hitherto, it is known that organic base substances, e.g. dyestuffs or dyes, have a tendency toward fading or discoloration. A number of reports have been submitted with respect to methods of reducing the fading or discoloration or methods of improving fastness to light. For instance, U.S. Pat. No. 3,432,300 describes an improvement in fastness to visible and UV light by mixing organic compounds, such as indophenol, indoaniline, azo and azomethine dyes, with phenolic compounds having fused heterocyclic rings.

In the field of silver halide photographic materials, azomethine dyes or indoaniline dyes are formed by reaction between oxidants of aromatic primary amine photographic developers and couplers as is particularly set forth in Chapter 17 of "The Theory of the Photographic Process, by C. E. Mees and T. H. James (Macmillan Pub. 1967)". A number of methods of improving light stability of images formed from these dyes or color images are known. For instance, there are known methods using hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028 and British Pat. No. 1,363,921, gallic acid derivatives as described in U.S. Pat. Nos. 3,457,079 and 3,069,262 and Japanese Patent Publication No. 13,496/1968, p-alkoxyphenols as described in U.S. Pat. Nos. 2,735,765 and 3,698,909, and derivatives such as chroman and coumaran as described in U.S. Pat. Nos. 3,432,300, 3,573,050, 3,574,627, 3,764,337, 3,574,626, 3,698,909 and 4,015,990. However, these compounds serve, more or less, as an inhibitor for fading or discoloration of color images but are not satisfactory.

British Pat. No. 1,451,000 describes a method of improving light stability of an organic base compound by the use of azomethine extinction compounds whose absorption maximum is larger than an absorption maximum of the organic base compound. However, this method is disadvantageous in that because the azomethine extinction compound is deeply colored, it greatly influences the hue of the base compound.

Use of metal complex salts for preventing optical deterioration of polymers is described in J. Polym. Sci., Polym. Chem. Ed., by J. P. Guillory and R. S. Becker, 12, 993 (1974) and J. Polym. Sci., Polym. Lett. Ed., by R. P. R. Ranaweera and G. Scott, 13, 71 (L975). A method for stabilizing dyes with metal complex salts is described in Japanese Patent Application (O.P.I.) No. 87,649/1975 and Research Disclosure 15162 (1976). However, these complexes do not a great fading-inhibiting effect and are not high with respect to solubility in organic solvents. Thus, it is not possible to add the complexes in amounts sufficient to cause the fading-inhibiting effect to be satisfactorily shown. Moreover, these complexes are deeply colored, so that if added in large amounts, they adversely influence the hue and purity of organic base substances, particularly dyes.

SUMMARY OF THE INVENTION

An object of the invention is to provide a method for improving light stability of organic base substances.

Another object of the invention is to provide a method for improving light stability of organic base substances and, particularly, dyestuffs or dyes without deterioration of their hue and purity.

A further object of the invention is to provide a method for improving light stability of organic infrared-absorptive substances.

A still further object of the invention to provide a method for improving light stability of organic base substances by the use of stabilizers for such organic base substances which have high solubility in organic solvent and a high miscibility with the organic base substances.

The present inventors made extensive studies in order to achieve the above objects and, as a result, have accomplished the method of the invention.

Other and further objects, features and advantages of the invention will appear more fully from the following description.

DETAILED DESCRIPTION OF THE INVENTION

The above objects can be attained by comprising an organic base substance having an absorption maximum at about 300 nm to about 1,500 nm in coexistence with at least one compound of the following general formula (I) or (II)

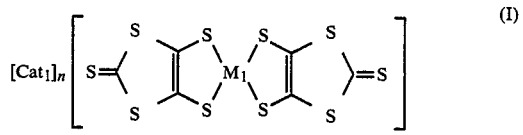

or

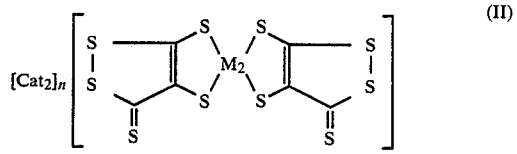

in which [Cat$_1$] and [Cat$_2$] represent, respectively, a cation necessary for neutralizing the complex, M$_1$ and M$_2$ represent, respectively, nickel, copper, palladium or platinum, and n is 1 or 2. The method of the invention is very effective for the purpose of improving the fastness of organic base substances to light.

In this specification and in the claims, the term "organic base substance" or "base compound" used herein is intended to mean substances which are visually observed as colored or colorless under irradiation of sunlight. More particularly, the substances include not only those substances which have an absorption maximum merely in a visible range, but also optical fluorescent brighteners or substances having an absorption maximum in an IR region. In the practice of the invention, the organic base substances also include organic substances whose absorption maximum ranges from about 300 nm in a UV region to about 1,500 nm in an IR region.

The term "dye" used herein includes color materials and dyestuffs and is intended to mean organic substances which are visually observed as colored under sunlight.

The term "light" used herein is intended to mean an electromagnetic wave of less than about 1,500 nm, which includes an UV ray of less than about 400 nm, visible light of from 400 nm to about 700 nm, and an IR ray of from about 700 nm to about 1,500 nm.

In the compounds of the above general formulae [I] and [II], the cations represented by [Cat$_1$] and [Cat$_2$] may be inorganic cations which include alkali metals such as, for example, Li, Na, K and the like, alkaline earth metals such as Mg, Ca, Ba and the like, and NH$_4^+$. Organic cations may also be used including a quaternary ammonium ion and a quaternary phosphonium ion.

Of these cations [Cat$_1$] and [Cat$_2$], preferable cations are those of the following general formulae (III-a), (III-b), (III-c), (III-d) and (III-e).

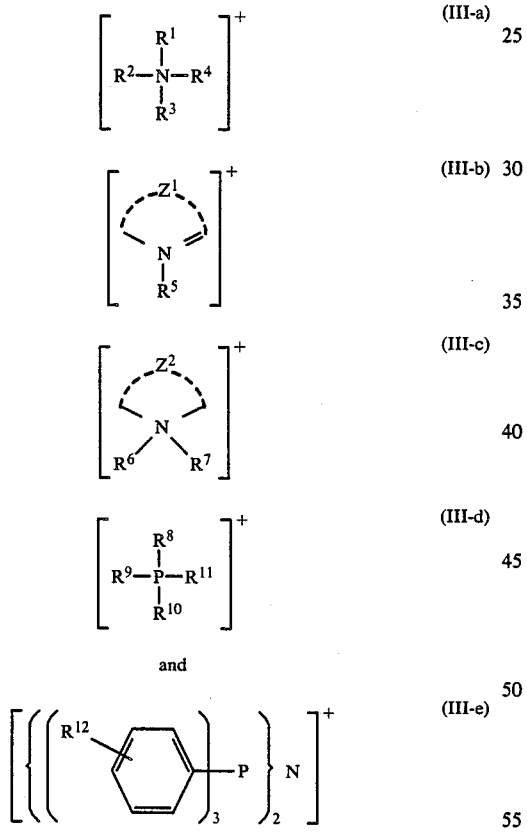

and in which R$^1$, R$^2$, R$^3$, R$^4$, R$^5$, R$^6$, R$^7$, R$^8$, R$^{10}$, R$^{11}$ and R$^{12}$ independently represent a substituted or unsubstituted alkyl group having from 1 to 20 carbon atoms or a substituted or unsubstituted aryl group having from 6 to 14 carbon atoms, Z$^1$ and Z$^2$ independently represent a non-metallic atom group to form a five-membered or six-membered ring along with a nitrogen atom in the respective formulae.

Examples of the substituted or unsubstituted alkyl group having from 1 to 20 carbon atoms include a methyl group, an ethyl group, an n-butyl group, an iso-amyl group, an n-dodecyl group, an n-octadecyl group and the like. Examples of the aryl group having from 6 to 14 carbon atoms include a phenyl group, a tolyl group, an alpha-naphthyl group and the like.

These alkyl groups or aryl groups may be further substituted with a cyano group a hydroxyl group, an alkyl group having from 1 to 20 carbon atoms (for example, a methyl group, an ethyl group, an n-butyl group, an n-octyl group or the like) an aryl group having from 6 to 14 carbon atoms (for example, a phenyl group, a tolyl group, an alpha-naphthyl group or the like) an acyloxy group having from 2 to 20 carbon atoms (for example, an acetoxy group, a benzoyloxy group, a p-methoxybenzoyloxy group or the like) an alkoxy group having from 1 to 6 carbon atoms (for example, a methoxy group, an ethoxy group, a propoxy group, a butoxy group or the like) an aryloxy group (for example, a phenoxy group, a tolyloxy group or the like) an aralkyl group (for example, a benzyl group, a phenetyl group, an anisil group or the like) an alkoxycarbonyl group (for example, a methoxycarbonyl group, an ethoxycarbonyl group, an n-butoxycarbonyl group or the like) an aryloxycarbonyl group (for example, a phenoxycarbonyl group, a tolyloxycarbonyl group or the like) an acyl group having from 2 to 21 carbon atoms (for example, an acetyl group, a benzoyl group or the like) an acylamino group (for example, an acetylamino group, a benzoylamino group or the like) a carbamoyl group (for example, an N-ethylcarbamoyl group, an N-phenylcarbamoyl group or the like) an alkylsulfonylamino group (for example, a methylsulfonylamino group, a phenylsulfonylamino group or the like) a sulfamoyl group (for example, an N-ethylsulfamoyl group, an N-phenylsulfamoyl group or the like) or a sulfonyl group (for example, a mesyl group, a tosyl group or the like).

As stated before, Z$^1$ and Z$^2$ independently represent a non-metallic atom group necessary for forming a five-membered ring or a six-membered ring. Examples or the five-membered ring and the six-membered ring include a pyridine ring, an imidazole ring, a pyrrole ring, a 2-pyrroline ring, a pyrrolidine ring, a piperidine ring, a pyrazole ring, a pyrazoline ring, an imidazoline ring and the like. The cations represented by the general formula (III-b) are, for example, a dodecylpyridinium group, a hexadecylpyridinium group, a dodecylimidazolium group and the like. The cations represented by the general formula (III-c) are an N-ethyl-N-hexadecylpiperidinium group, an N-ethyl-N-dodecylpirazolinium group and the like.

Of the cations of the general formulae (III-a), (III-b), (III-c), (III-d), and (III-e) preferable cations are those of the formulae (III-a), (III-b), (III-d) and (III-e) in view of the ease in availability of starting materials for the preparation and the production costs.

The solubility of the compounds of the general formulae [I] and [II] in organic solvents is influenced by the type of cation, e.g. [Cat$_1$] or [Cat$_2$].

In general, when the substituent bonded to the quaternary hetro-atom is an alkyl group, the solubility becomes higher as the chain length is larger. This tendency becomes more pronounced in the case of tetraalkyl-substituted ammonium or phosphonium. High solubility is ensured in the case of ammonium cations whose carbon atoms are 17 or over in total and phosphonium cations whose carton atoms are 4 or over in total.

In the compounds of the general formulae [I] and [II], nickel cobalt, copper, palladium and platinum represented by $M_1$ and $M_2$ are preferably used in this order.

The metal complexes of the general formulae [I] and [II] have a plane four-coordinate stereostructure. It will be noted that although it is not unconditionally determined whether the thioketone group of the compounds of the general formula [II] is symmetric or asymmetric with respect to the central metal, these compounds are represented in the practice of the invention as by the general formula [II] for convenience' sake.

The compound of general formula [I] or [II] per se is disclosed in the copending application Ser. No. 754,759, filed on July 15, 1985 (Japanese Patent Application (OPI) No. 26686/1986) as an infrared absorbent.

The compounds of the general formulae [I] and [II] can be prepared as follows.

The compound of the general formula [I] (n=2) is obtained by reacting carbon disulfide with sodium, converting the resulting disodium-1,3-ditiol-2-thion-4,5-dithiolate into a zinc complex, causing the complex to react with benzoyl chloride to obtain a bisbenzoylthio product. This product is decomposed with an alkali and then reacted with a metal salt to obtain the intended compound.

The compound of the general formula [I] (n=1) is obtained by oxidizing the thus obtained complex (n=2) with a suitable oxidizing agent.

The compounds of the general formula [II] (n=2) are obtained by heating to about 130° C. disodium-1,3-dithio-2-thione-4,5-ditholate obtained by reaction between carbon disulfide and sodium for isomerization into disodium-1,2-dithiol-3-thione-4,5-dithiolate. This compound is converted into a zinc complex and reacted with benzoyl chloride to obtain a bisbenzoylthio product. This product is decomposed with an alkali and reacted with a metal salt to obtain the intended compound.

The compound of the general formula [II] (n=1) is obtained by oxidizing the thus obtained complex (n=2) with a suitable oxidizing agent.

The 1,3-dithiol-2-thione-4,5-dithiolate anion which is an intermediate for obtaining the compound of the general formula [I] or [II] may be obtained by electrochemical reduction aside from the above reduction method using Na.

Of the compounds of the general formulae [I] and [II], preferable compounds are shown below, but they should not be construed as limiting the compounds of the general formulae [I] and [II] to those compounds.

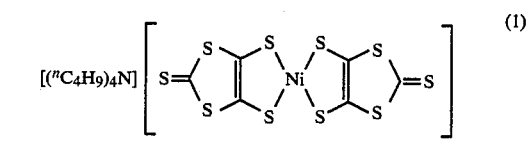
(1)

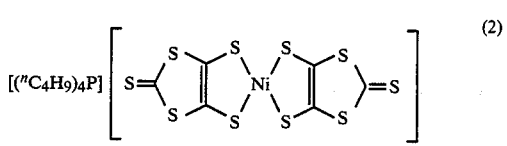
(2)

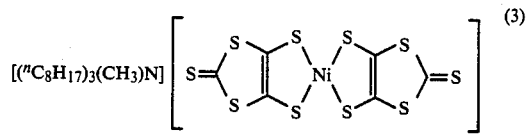
(3)

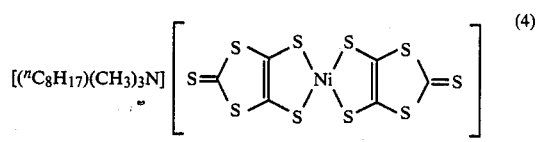
(4)

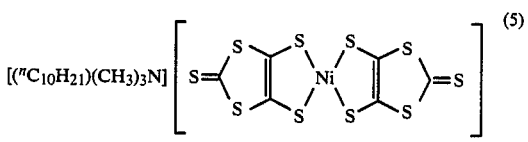
(5)

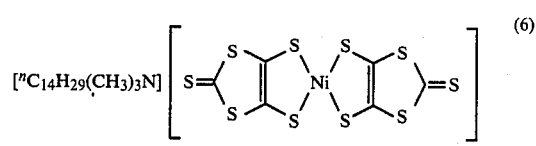
(6)

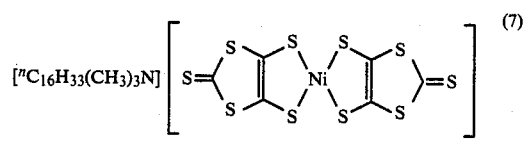
(7)

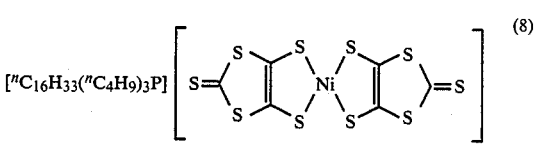
(8)

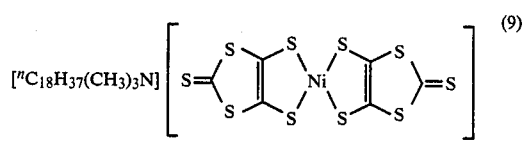
(9)

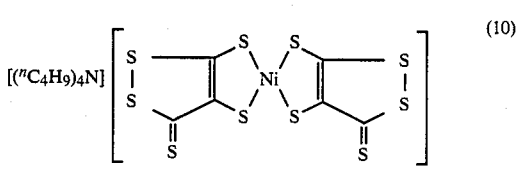
(10)

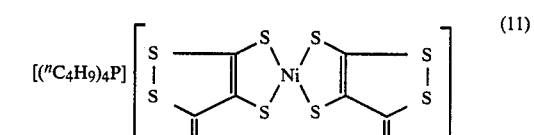
(11)

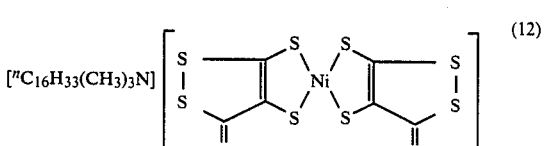
(12)

-continued
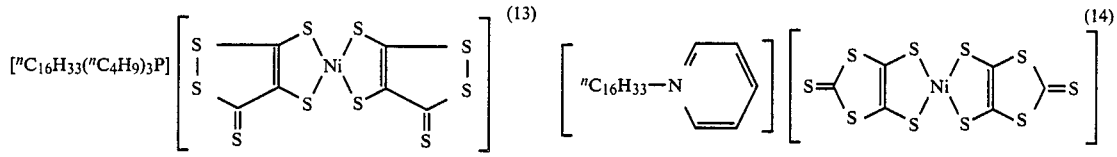
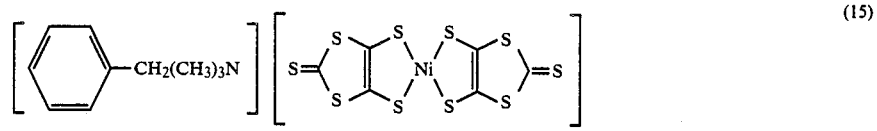
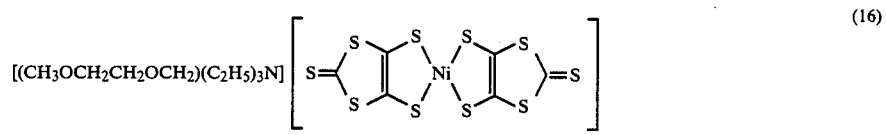
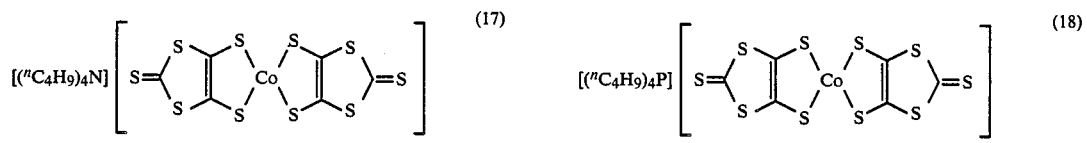
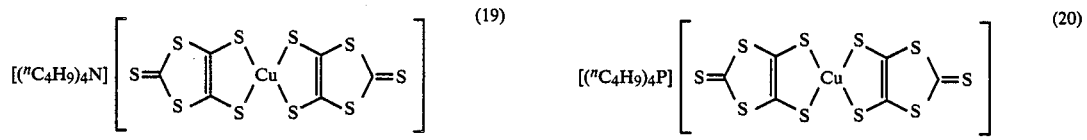
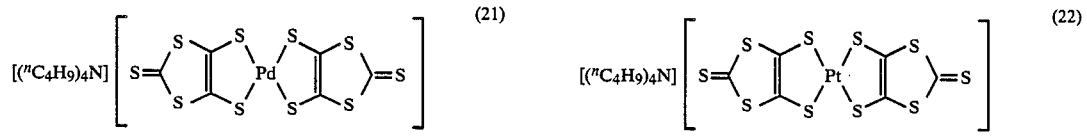
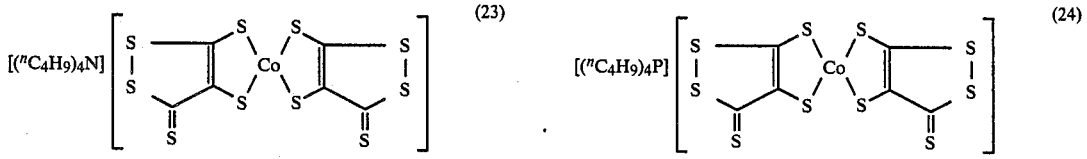
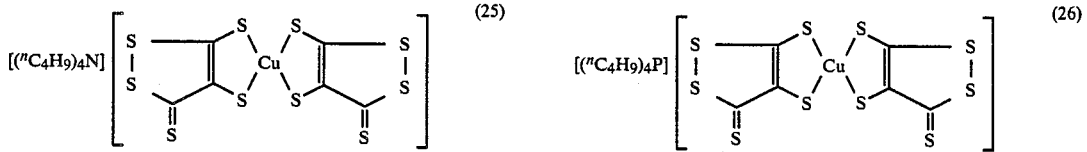
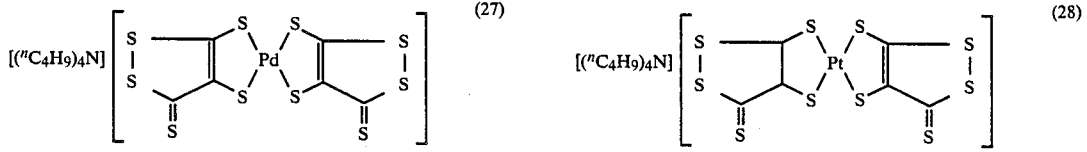
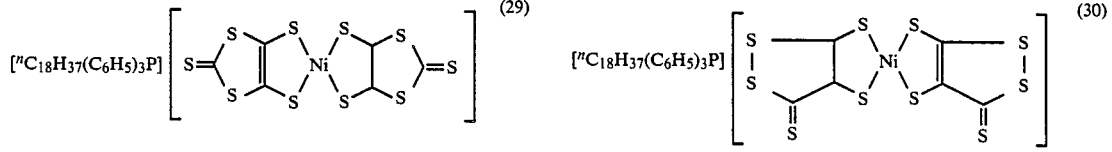

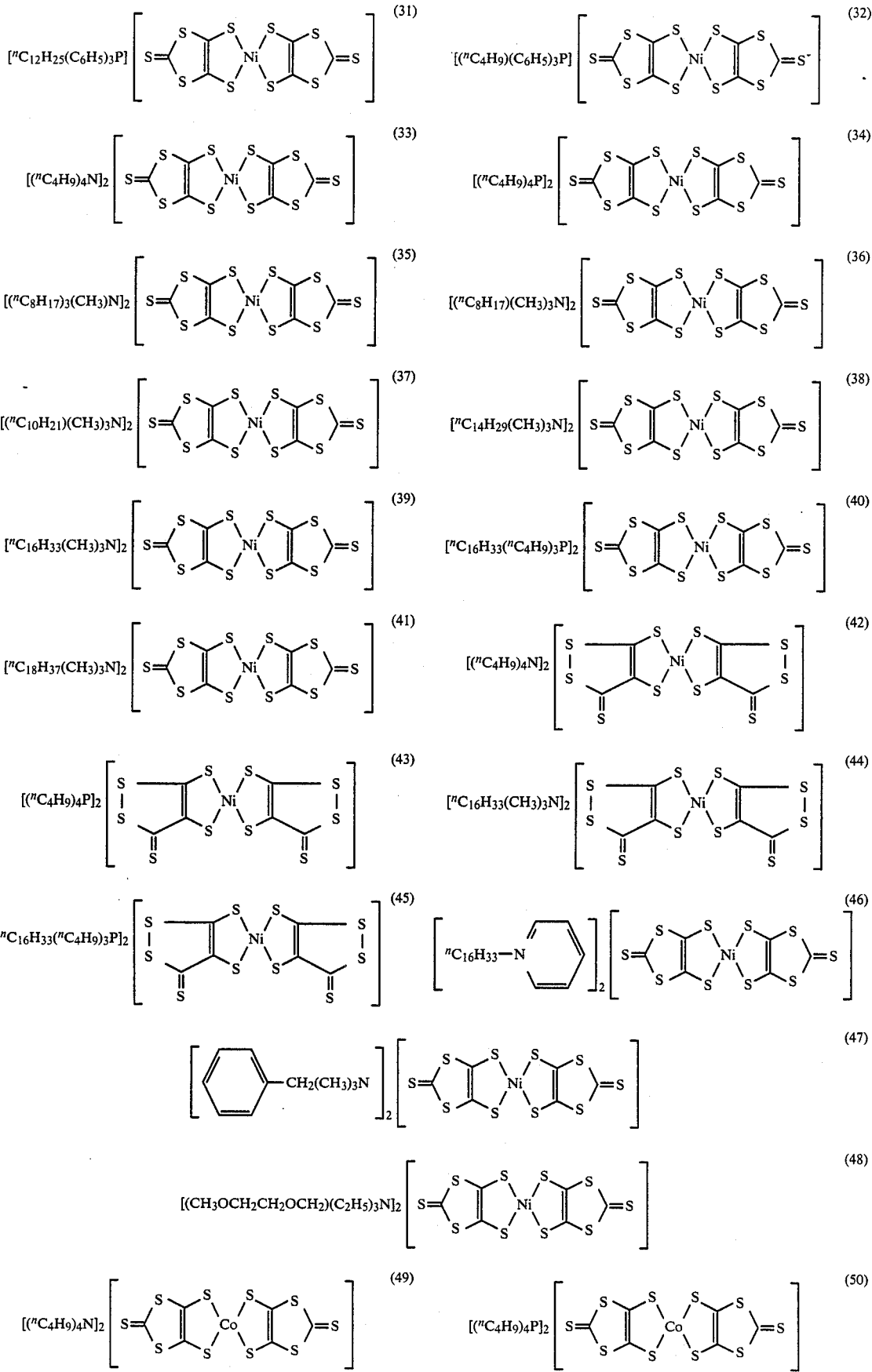

-continued
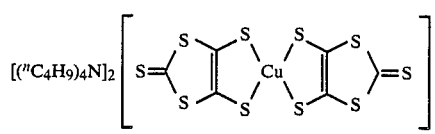 (51)
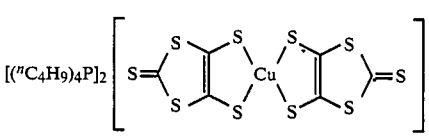 (52)
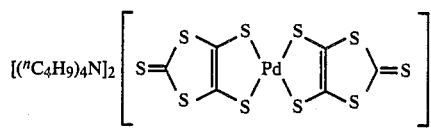 (53)
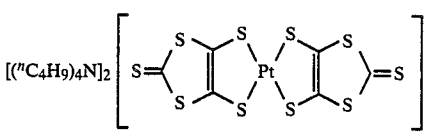 (54)
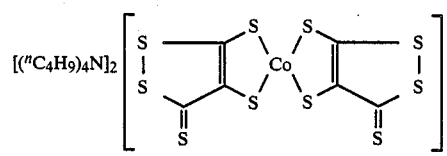 (55)
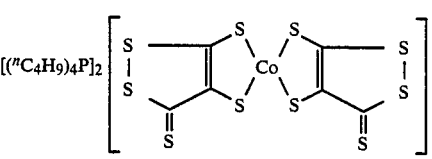 (56)
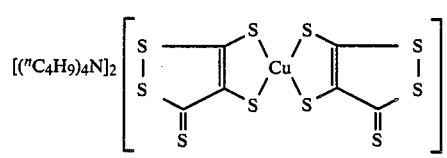 (57)
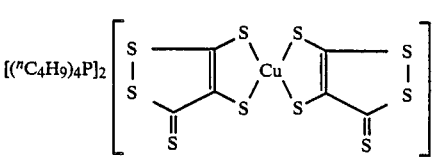 (58)
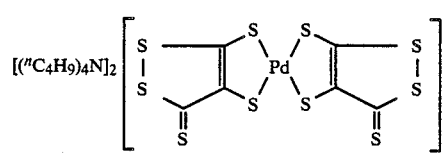 (59)
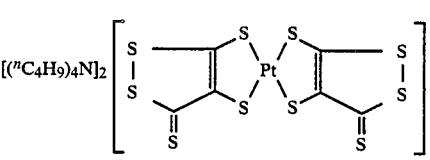 (60)
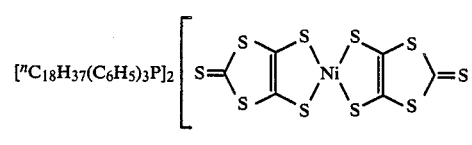 (61)
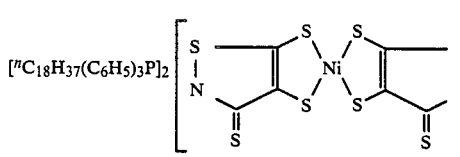 (62)
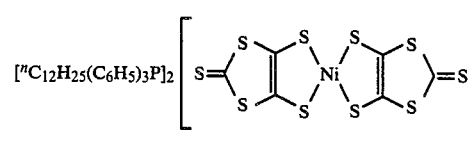 (63)
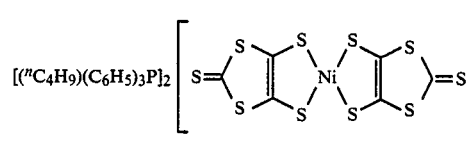 (64)
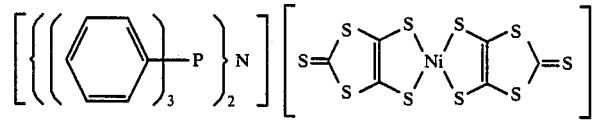 (65)
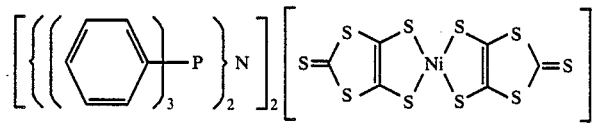 (66)
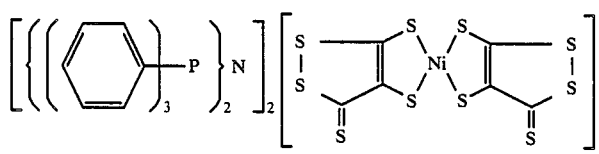 (67)
The organic base substances according to the invention include substantially all dyes classified as having dyeing properties, e.g. water-soluble dyes such as basic dyes, acid dyes, direct dyes, soluble vat dyes and mordant dyes, insoluble dyes such as sulur dyes, vat dyes oil colors, disperse dyes, azoic dyes and oxidation dyes and reactive dyes. These organic base substances include not only dyes which are observed as colored under irradiation of sunlight, but also fluorescent brightening dyes which are colorless or light yellow in color.

Of these dyes, preferable dyes include, upon classification through a chemical structure, quinoneimine dyes such as azine dyes, oxazine dyes, thiazine dyes and the like, methine and polymethine dyes such as cyanine dyes, merocyanine dyes, azomethine dyes and the like, azo dyes, anthraquinone dye, naphthoquinone dyes, indoamine dyes, indoaniline and indophenol dyes, indigoid dyes, carbonium dyes, formazan dyes and the like.

More preferable dyes used as the organic base substance of the invention include anthraquinone, naphthoquinone, quinoneimineazo, methine, polymethine, azomethine, indoamine, indoaniline, indophenol and formazan dyes.

More preferable dyes used in the present invention are anthraquinone, naphthoquinone, quinoneimineazo, methine, polymethine, azomethine, indoamine, indoaniline and indophenol dyes.

Specific examples of the dyes used as the base substance of the invention are those indicated below, but these dyes should not be construed as limiting the present invention.

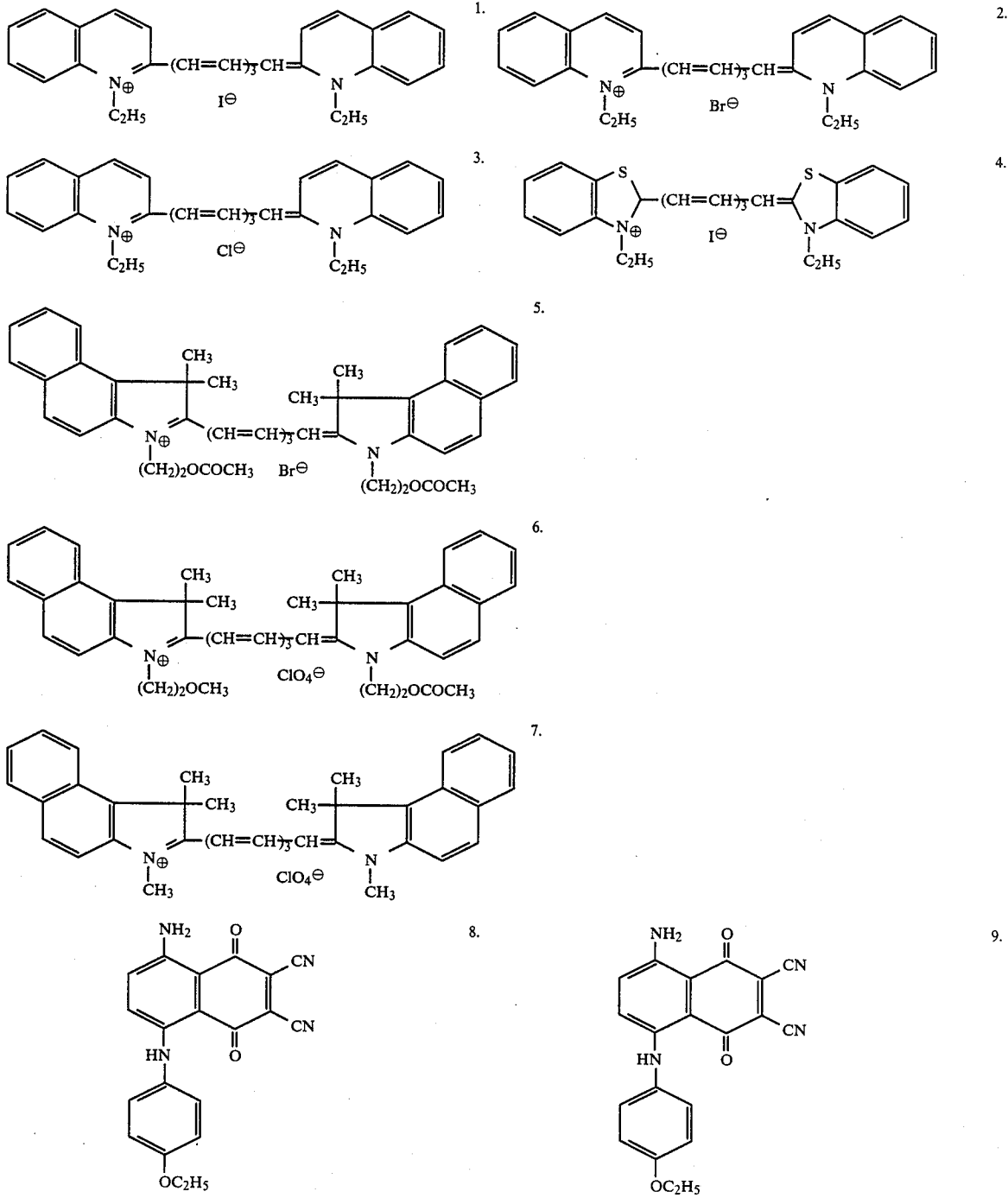

10.

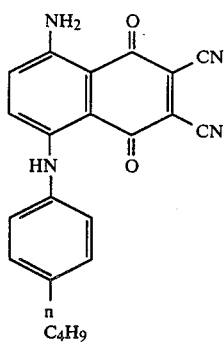

11.

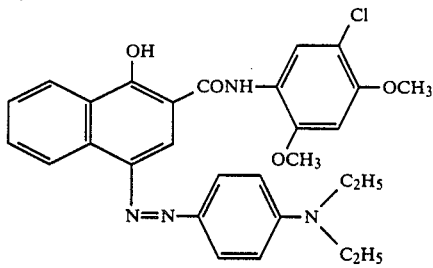

As described before, the metal complexes used in the present invention stabilize organic base substances. The stabilizing effect may be shown when a metal complex and an organic base substance are uniformly dispersed in a suitable medium or binder.

Examples of the medium or binder may be polymer substances such as plastic resins.

Such polymer substances include, for example, polyesters typical of which is polyethylene terephthalate, cellulose esters such as cellulose diacetate, cellulose triacetate, cellulose acetate butyrate and the like, polyolefins such as polyethylene, polypropylene and the like, polyvinyl compounds such as polyvinyl chloride, polyvinylidene chloride, vinyl chlride-vinyl acetate copolymers, polystyrene and the like, acrylic addition polymers such as polymethyl methacrylate, polycarbonates such as polycarbonic acid esters, phenolic resins, urethane resins, and hydrophilic binders such as gelatin. Preferable mediums or binders are indicated below.

(i) Polyolefins: polyethylene, polypropylene, poly-4-methylpentene-1

(ii) Polyolefin copolymers: ethylene-vinyl acetate copolymers, ethylene acrylate copolymers, ethylene-acrylic acid copolymers, ethylene-propylene copolymers, ethylene-butene-1 copolymers, ethylene-maleic anhydride copolymers, ethylene-propylene terpolymers (EPT).

In the above copolymers, the ratio of the respective co-monomers may be arbitrarily determined.

(iii) Vinyl chloride copolymers: vinyl acetate-vinyl chloride copolymers, vinyl chloride-vinylidene chloride copolymers, vinyl chloride-maleic anhydride copolymers, copolymers of acrylic esters or methacrylic esters and vinyl chloride, acrylonitrile-vinyl chloride copolymers, vinyl chloride-ether copolymers, copolymers of ethylene or propylene and vinyl chloride, ethylene-vinyl acetate copolymers graft-copolymerized with vinyl chloride and the like. In this case, the ratio of monomers for the copolymerization may be arbitrarily determined.

(iv) Vinylidene chloride copolymers: vinylidene chloride-vinyl chloride copolymers, vinylidene chloride-vinyl chloride-acrylonitrile copolymers, vinylidene chloride-butadiene-vinyl halide copolymers, and the like.

In this case, the ratio of monomers for the copolymerization may be arbitrarily determined.

(v) Polystyrene.

(vi) Styrene copolymers: styrene-acrylonitrile copolymers (AS resins), styrene-acrylonitrile-butadiene copolymers (ABS resins), styrene-maleic anhydride copolymers (SMA resins), styrene-acrylic ester-acrylamide copolymers, styrene-butadiene copolymer (SBR), styrene-vinylidene chloride copolymers, styrene-methyl methacrylate copolymers, and the like.

The ratio of monomers for the copolymerization may be arbitrarily determined.

(vii) Styrene type polymers: polymers of α-methylstyrene, p-methylstyrene, 2,5-dichlorostyrene, α,β-vinylnaphthalene, α-vinylpyridine, acenaphthene, vinylanthracene and the like, and copolymers of these monomers such as, for example, copolymers of α-methylstyrene and methacrylic esters.

(viii) Cumarone-indene resins: cumarone-indenestyrene copolymers.

(ix) Terpene resin and picolite: a terpene polymer which is a polymer of limonene obtained from α-pinene and picolite obtained from β-pinene.

(x) Acrylic resins: those resins have an atomic group of the following formula are preferred

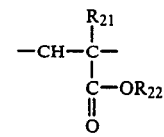

wherein $R_{21}$ represents a hydrogen atom or an alkyl group and $R_{22}$ represents a substituted or unsubstituted alkyl group. In the above formula, $R_{21}$ more specifically represents a hydrogen atom or a lower alkyl group having from 1 to 4 carbon atoms and, preferably, a hydrogen atom or a methyl group.

$R_{22}$ may be either a substituted or unsubstituted alkyl group. Preferably, the alkyl group has from 1 to 8 carbon atoms. When $R_{22}$ represents a substituted alkyl group, the substituent should preferably be a hydroxyl group, a halogen atom or an amino group, particularly a dialkylamino group.

The atomic group of the above formula may constitute a variety of acrylic resins along with other types of recurring units. In general, acrylic resins are composed of homopolymers or copolymers having recurring units of one or more atomic groups of the above formula.

(xi) Polyacrylonitrile.

(xii) Acrylonitrile copolymers: acrylonitrile-vinyl acetate copolymers, acrylonitrile-vinyl chloride copolymers, acrylonitrile-styrene copolymers, acrylonitrile-vinylidene chloride copolymers, acrylonitrile-vinylpyridine copolymers, acrylonitrile-methyl methacrylate copolymers, acrylonitrile-butadiene copolymers, acrylonitrile-butyl acrylate copolymers and the like.

In this case, the ratio of monomers for the copolymerization may be arbitrarily determined.

(xiii) Diacetone acrylamide polymer obtained by reacting acetone with diacetone acrylamide polymeracrylonitrile.

(xiv) Polyvinyl acetate.

(xv) Vinyl acetate copolymers: copolymers with acrylic esters, vinyl ethers, ethylene, vinyl chloride and the like.

(xvi) Polyvinyl ethers: polyvinyl methyl ether, polyvinyl ethyl ether, polyvinyl butyl ether and the like.

(xvii) Polyamides: homonylons such as nylon 6, nylon 6-6, nylon 6-10, nylon 6-12, nylon 9, nylon 11, nylon 12, nylon 12 (tradenames) and the like, copolymers such as nylon 6/6-6/6-10, nylon 6/56-6/12. nylon 6/6-6/11 (tradenames) and the like, and modified nylons, if desired.

(xviii) Polyesters: polycondensates or copolycondensates of various dibasic acids including aliphatic dibasic acids such as oxalic acid, succinic acid, maleic acid, adipic acid, sebacic acid and the like and aromatic dibasic acids such as isophthalic acid, terephthalic acid and the like and glycols such as ethylene glycol, tetramethylene glycol, hexamethylene glycol and the like are preferred.

Of these, polycondensates of aliphatic dibasic acids and glycols and copolycondenstates of glycols and aliphatic dibasic acids are more preferable.

Moreover, a modified glyptal resin (polycondensate of phthalic anhydride and glycerine is modified by esterification with fatty acids or natural resins.) is also preferably used.

(xix) Polyvinyl acetal resins.

Polyvinyl formal and polyvinyl acetal resins which are obtained by acetalization of polyvinyl alcohol are all preferably used.

The degree of acetalization of the polyvinyl acetal resin may be arbitrarily determined.

(xx) Polyurethane resins: thermoplastic polyurethane resins having urethane bonds.

Polyurethane resins obtained by condensation between glycols and diisocyanates and, particularly, polyurethane resins obtained by condensation between alkylene glycols and alkylene diisocyanates are preferred.

(xxi) Polyethers: styrene-formalin resins, ring-opened polymers of cyclic acetals, copolymers of polyethylene oxide and glycols, polypropylene oxide and glycols, propylene oxide-ethylene oxide, polyphenylene oxides and the like.

(xxii) Cellulose derivatives: cellulose esters and ethers such as nitro cellulose, acetyl cellulose, ethyl cellulose, acetyl butyl cellulose, hydroxyethyl cellulose, hydroxypropyl cellulose, methyl cellulose, ethylhydroxyethyl cellulose and the like, and mixtures thereof.

(xxiii) Polycarbonates: various polycarbonates such as polydioxydiphenylmethane carbonate, dioxydiphenylpropane carbonate and the like.

(xxiv) Ionomers: Na, Li, Zn and Mg salts of methacrylic acid and acrylic acid.

(xxv) Ketone resins: polycondensates of cyclic ketones such as cyclohexanone, acetophenone and the like and formaldehyde.

(xxvi) Xylene resins: polycondensates of m-xylene or mesitylene and formalin, or modified products thereof.

(xxvii) Petroleum resins: $C_5$ resins, $C_9$ resins, $C_5$–$C_9$ copolymers, dicyclopentadiene resins, or copolymers of these monomers or modified products thereof.

(xxviii) Blends of two or more kinds of (i)–(xxvii), or blends with other thermoplastic resins.

In order to disperse the metal complexes uniformly in a medium or binder, the metal complexes may be preferably dissolved previously in low-boiling solvent such as alkyl halides (e.g., chloroform, dichloromethane) alcohols (e.g., methanol, ethanol, isopropanol, butanol)ethers (e.g., dimethyl ether, ethyl methyl ether, diethyl ether, 1-ethoxypropane)glycols (e.g., 1,2-ethanediol, 1,2-propanediol 1,3-propanediol)ketones (e.g., acetone, ethyl metyl ketone 3-pentanone)esters (e.g., ethyl formate, methyl acetate, ethyl acetate) and amides (e.g., formamide, acetamide, succinamide). Then the metal complex dissolved in the solvent may be added to the medium or binder together with the organic base substance.

If used in any amounts, the metal complex described above will bring about an improvement of the invention. Because the metal complex which is used in excess does not impede the product except that the product is objectionably colored, with respect to its upper limit the amount of the metal complex is not theoretically critical.

Preferably, based on the organic base substance, at least 0.1 mole percent of metal complex is used and an amount not less than 1 mole percent is more preferable. With the increase of amount the stabilizing effect of metal complex is enhanced. There is not any upper limit but in practice a hundred thousand moles percent or less of metal complex is used based on the organic substance.

These metal complexes may be used in combination with UV absorbers such as Tinuvin (tradename, merchandized by CIba-Geigy AG, Swiss), hydroquinone and the like.

To further illustrate this invention, and not by way of limitation, the following examples are given.

EXAMPLE 1

Preparation of Exemplified Compound (34)

(1—1) Preparation of bis(tetraethylammonium)-bis(1,3-dithiol-2-thione-4,5-dithiolato)zinc complex:

The reaction operations were all effected in an argon atmosphere. 23 g of sodium was cut into pieces and dispersed in 180 ml of carbon disulfide, after which 200 ml of dimethylformamide was gently added to dropwise with agitation. Care was taken in order that heat did not violently generate. After completion of the dropping of the dimethylformamide, the mixture was gently heated with care and refluxed for 24 hours. After completion of the reaction, unreacted sodium was removed by filtration. Thereafter, 50 ml of ethanol was added to the filtrate and agitated at room temperature for 2 hours. The carbon disulfide was distilled off from the solution under reduced pressure at room temperature. Subsequently, into the solution 300 ml of water was gradually added dropwise, followed by subjecting the resulting solution to filtration.

A solution, which has been prepared by dissolving 20 g of zinc chloride in 500 ml of methanol and adding 500 ml of a concentrated aqueous ammonia to the solution, was added to the above reaction solution at room temperature and agitated for 5 minutes. When an aqueous solution of 53 g of tetraethylammonium bromide in 250 ml of water was added, a red precipitate was immediately deposited, followed by filtration and air-drying to give the captioned zinc complex.

(1-2) Preparation of 4,5-bis(benzoylthio)-1,3-dithiol-2-thione:

22 g of the zinc complex obtained in (1-1) was dissolved in 500 ml of acetone and filtered. While the filtrate was agitated, 150 ml of benzoyl chloride was added. Immediately, a yellow precipitate was deposited. After filtration and washing with water, the precipitate was air-dried to obtain 16 g of the captioned compound.

(1-3) Preparation of Exemplified Compound (34).

9.2 g of the bis(benzoylthio) product obtained in (1-2) was dissolved in 50 ml of methanol, to which 6.3 g of a 28% methanol solution of sodium methoxide was added, followed by agitation for 10 minutes. A solution of 2.4 g of nickel chloride hexahydrate in 50 ml of methanol was added to the solution and agitated at room temperature for 30 minutes. To the solution was further added a solution of 8.5 g of tetrabutylphosphonium bromide in 100 ml of methanol, whereupon a black precipitate was deposited immediately, followed by agitation for 20 minutes, filtration, washing with acetone, air-drying and recrystallization from acetone-isopropyl alcohol to give the captioned compound with a yield of 3.8 g.

EXAMPLE 2

Preparation of Exemplified Compound (2)

One gram of the nickel complex obtained in (1-3) was dissolved in 60 ml of acetone, to which 30 ml of acetic acid was added, followed by agitation for 3 hours and removal of the solvent by distillation to give black crystals. The crystals were recrystallized from acetone-methanol to obtain the intended exemplified compound (2). Yield 0.4 g, m.p. 185° C., $\lambda$max: 1125 nm, $\epsilon$max: $2.51 \times 10^4$ (in $CH_2Cl_2$).

EXAMPLE 3

Preparation of Exemplified Compound (42)

(1-1) Preparation of bis(tetraethylammonium)-bis(1,2-dithiol-3-thione-4,5-dithiolato)zinc complex:

The reaction operations were all effected in an argon atmosphere. 25 g of sodium was cut into pieces and dispersed in 180 ml of carbon disulfide, into which 200 ml of dimethylformamide was gently added to dropwise with agitation. At that time, care was taken in order that heat did not violently generate. After completion of the dropping of the dimethylformamide, the mixture was gently heated with care and refluxed for 24 hours. After completion of the reaction, unreacted sodium was removed by filtration and the carbon disulfide was distilled off from the filtrate at room temperature under reduced pressure. The resulting solution was agitated on an oil bath at 140° C. for 2 hours and further agitated at room temperature or 2 hours, followed by gently adding 300 ml of water. The resulting solution was filtered.

A preliminarily prepared solution, which was obtained by dissolving 20 g of zinc chloride in 500 ml of methanol and adding 500 ml of a concentrated aqueous ammonia to the solution, was added to the above reaction solution at room temperature and agitated for 5 minutes. When an aqueous solution of 53 g of tetraethylammonium bromide in 250 ml of water was added, a red precipitate was immediately deposited. The precipitate was separated by filtration followed by air-drying to give the captioned zinc complex.

(1-2) Preparation of 4,5-bis(benzoylthio)-1,2-dithiol-3-thione:

18 g of the zinc complex obtained in (1-1) was dissolved in 500 ml of acetone and filtered. While the filtrate was agitated, 150 ml of benzoyl chloride was added. Immediately, a yellow precipitate was deposited. After filtration and washing with water, the precipitate was air-dried to give 12 g of the captioned compound.

(1-3) Preparation of Exemplified Compound (42).

9.2 g of the bis(benzoylthio) product obtained in (1-2) was dissolved in 50 ml of methanol. Into the solution 6.3 g of a 28% methanol solution of sodium methoxide was added, followed by agitation for 10 minutes. A solution of 2.4 g of nickel chloride hexahydrate in 50 l of methanol was then added to the solution and agitated at room temperature for 30 minutes. To the solution was further added a solution of 7.5 g of tetrabutylammonium bromide in 100 ml of methanol, whereupon a black precipitate was deposited immediately. After agitation for 20 minutes, the precipitate was separated by filtration, followed by washing with acetone and air-drying. Recrystallization from acetone-isopropyl alcohol resulted in the captioned compound. Yield 2.8 g.

EXAMPLE 4

Preparation of Exemplified Compound (10)

One gram of the nickel complex obtained in (1-3) was dissolved in 60 ml of acetone, to which 30 ml of acetic acid was added followed by agitation for 3 hours and removal of the solvent by distillation to separate black crystals. The crystals were recrystallized from acetone-methanol to obtain the intended exemplified compound (10). Yield 0.39 g, m.p. 270° C., $\lambda$max: 1138 nm, $\epsilon$max: $2.50 \times 10^4$ (in $CH_2Cl_2$).

EXAMPLE 5

Dimethylformamide solutions (20 ml) of various kinds of base dyes in presence of metal complexes were subjected to a fading test. Prior to light irradiation, these solutions had $2 \times 10^{-4}$ moles of base dyes and $6 \times 10^{-4}$ moles of metal complexes dissolved therein.

Light exposure was effected using a xenon lamp (200,000 luxes) with UV cut-filter Exposure time was 200 hours.

The results are shown in table I.

TABLE I

| Sample No. | Base Dye | Metal Complex | Residual Rate of Dye (%) | *Blank (%) |
|---|---|---|---|---|
| 1 | 1 | (1) | 78 | 0 |
| 2 | 2 | (1) | 85 | 0 |
| 3 | 3 | (33) | 66 | 0 |
| 4 | 4 | (33) | 76 | 0 |
| 5 | 7 | (33) | 76 | 0 |
| 6 | 8 | (33) | 94 | 68 |

*Residual rate of a dye when exposed without addition of any metal complex.

As is evident from the results, according to the method of this invention residual rates of the base dyes were remarkably enhanced.

EXAMPLE 6

Employing exemplified compound (1) or (33), compositions containing the respective ingredients as shown below were prepared. After mixing the ingredients, they were subjected to filtration and applied onto a metallic support by casting to form a film respectively, and each film was peeled to give a 25 μm thick film.

The resultant films were each irradiated with a xenon lamp (200,000 luxes) to determine a residual rate of the dye.

| Composition: | parts by weight |
| --- | --- |
| TAC (cellulose triacetate) | 170 parts |
| TPP (triphenyl phosphate) | 10 parts |
| Methylene chloride | 800 parts |
| Methanol | 160 parts |
| Exemplified compound (1) or (33) | 2 parts |
| Base dyes | 1 part |

TABLE II

| Sample No. | Base Dye | Metal Complex | Residual Rate of Dye (%) | *Blank (%) |
| --- | --- | --- | --- | --- |
| 7 | 1 | (1) | 96 | 36 |
| 8 | 2 | (1) | 93 | 38 |
| 9 | 3 | (33) | 93 | 41 |
| 10 | 4 | (33) | 95 | 40 |
| 11 | 7 | (33) | 91 | 35 |
| 12 | 8 | (33) | 98 | 92 |
| 13 | 1 | (43) | 87 | 36 |

*Residual rate of a dye when exposed without addition of any metal complex.

As is evident from the results of Sample Nos. 7~11 and 13 residual rates of the base dyes were remarkably improved. According to the result of Sample No. 12 even in the case of base dye 8 having good fastness to light, the residual rate was significantly improved.

Having described a specific embodiment of our bearing, it is believed obvious that modification and variation of our invention is within the scope of the present invention in view of the above teachings.

What I claim is:

1. A method for stabilizing an organic base substance to light which comprises causing an organic base substance having an absorption maximum in a range of about 300 nm to about 1,500 nm to coexist with at least one complex of the following general formula [I] or [II]

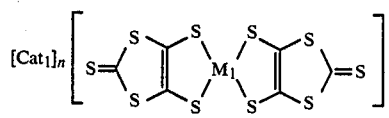

[I]

or

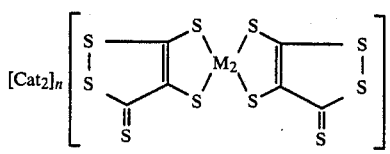

[II]

wherein [Cat$_1$] and [Cat$_2$] independently represent a cation necessary for neutralization of the complex, M$_1$ and M$_2$ independently represent nickel, copper, cobalt, palladium or platinum, and n is 1 or 2.

2. The method for stabilizing an organic base substance to light as in claim 1, wherein said organic base substance is a dye.

3. The method for stabilizing an organic base substance to light as in claim 2, wherein said dye is selected from the group consisting of water-soluble dyes, insoluble dyes and reactive dyes.

4. The method for stabilizing an organic base substance to light as in claim 1, wherein said dye is selected from the group consisting of quinoneimine dyes, methine and polymethine dyes, azo dyes, anthraquinone dyes, naphthoquinone dyes, indoamine dyes, indoaniline and indophenol dyes, indigoid dyes, carbonium dyes and formazan dyes.

5. The method for stabilizing an organic base substance to light as in claim 1, wherein said organic base substance and said metal complex are dispersed in a medium or binder.

6. The method for stabilizing an organic base substance to light as in claim 5, wherein said medium or binder is selected from the group consisting of polyesters, cellulose esters, polyolefins, polyvinyl compounds, acrylic addition polymers, polycarbonates, phenolic resins, urethane resins and hydrophilic binders.

7. The method for stabilizing an organic base substance to light as in claim 1, wherein said [Cat$_1$] or [Cat$_2$] is selected from the group consisting of a quaternary ammonium ion and a quaternary phosphonium ion.

8. The method for stabilizing an organic base substance to light as in claim 1, wherein said [Cat$_1$] or [Cat$_2$] is selected from the group consisting of the cations represented by the general formulae

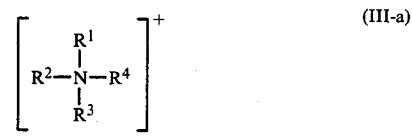

(III-a)

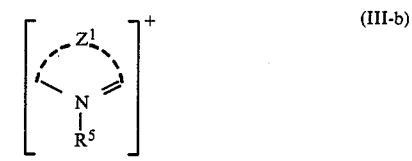

(III-b)

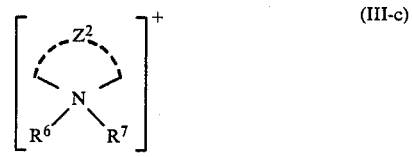

(III-c)

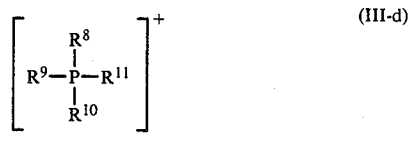

(III-d)

and

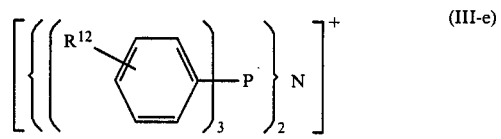

(III-e)

in which R$^1$, R$^2$, R$^3$, R$^4$, R$^5$, R$^6$, R$^7$, R$^8$, R$^{10}$, R$^{11}$ and R$^{12}$ independently represent a substituted or unsubstituted alkyl group having from 1 to 20 carbo atoms or a substituted or unsubstituted aryl group having from 6 to 14 carbon atoms, Z$^1$ and Z$^2$ independently represent a non-metallic atom group to form a five-membered or six-membered ring along with a nitrogen atom in the respective formulae.

9. The method for stabilizing an organic base substance to light as in claim 1, wherein $M_1$ and $M_2$ is selected from the group consisting of nickel, cobalt and copper.

10. The method for stabilizing an organic base substance to light as in claim 1, wherein at least 0.1 mol percent of metal complex is used based on the organic base substance.

11. The method for stabilizing an organic base substance to light as in claim 1, wherein said [Cat$_1$] or [Cat$_2$] is selected from the group consisting of alkali metals and alkaline earth metals.

12. The method for stabilizing an organic base substance to light as in claim 8, wherein the substituted or unsubstituted alkyl group having from 1 to 20 carbon atoms is selected from the group consisting of a methyl group, an ethyl group, an n-butyl group, an iso-amyl group, an n-dodecyl group, and a n-octadecyl group.

13. The method for stabilizing an organic base substance to light as in claim 8, wherein the aryl group having from 6 to 14 carbon atoms is selected from the group consisting of a phenyl group, a tolyl group, and an alpha-naphthyl group.

14. The method for stabilizing an organic base substance to light as in claim 8, wherein the five-membered ring or the six-membered ring are selected from the group consisting of a pyridine ring, an imidazole ring, a pyrrole ring, a 2-pyrroline ring, a pyrrolidine ring, a piperidine ring, a pyrazole ring, a pyrazoline ring, and an imidazoline ring.

15. The method for stabilizing an organic base substance to light as in claim 8, wherein the cations represented by the general formula (III-b) are selected from the group consisting of a dodecylpyridinium group, a hexadecylpyridinium group, and a dodecylimidazolium group.

16. The method for stabilizing an organic base substance to light as in claim 8, wherein the cations represented by the general formula (III-c) are selected from the group consisting of an N-ethyl-N-hexadecylpiperidinium group, and an N-ethyl-N-dodecylpirazolinium group.

* * * * *